US006210375B1

(12) United States Patent
Moulton et al.

(10) Patent No.: US 6,210,375 B1
(45) Date of Patent: Apr. 3, 2001

(54) NEEDLE RETRACTION MECHANISM WITH CONTROLLED RETRACTION SPEED

(75) Inventors: William G. Moulton, West Jordan; Gregory Quickel, Salt Lake City; Greg L. Brimhall, West Jordan, all of UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/252,299

(22) Filed: Feb. 19, 1999

Related U.S. Application Data

(63) Continuation of application No. 09/164,237, filed on Sep. 30, 1998, now abandoned.

(51) Int. Cl.[7] ................................................. A61M 5/32
(52) U.S. Cl. ........................................... 604/195; 604/236
(58) Field of Search ..................................... 604/192, 198, 604/195, 110, 203, 164.02, 164.04, 164.12, 171, 236; 600/578, 579

(56) References Cited

U.S. PATENT DOCUMENTS

| | | |
|---|---|---|
| 4,828,548 | 5/1989 | Walter . |
| 5,176,640 | 1/1993 | Nacci et al. . |
| 5,487,734 | 1/1996 | Thorne et al. . |
| 5,591,138 * | 1/1997 | Vaillancourt ..................... 604/198 X |
| 5,702,367 | 12/1997 | Cover et al. . |
| 5,713,873 * | 2/1998 | Jehle ................................... 604/198 |

FOREIGN PATENT DOCUMENTS 2675999    11/1992   (FR) .

OTHER PUBLICATIONS

International Search Report of PCT/US99/22454 which is the PCT counterpart to the pending application.

* cited by examiner

Primary Examiner—A. T. Nguyen
(74) Attorney, Agent, or Firm—Eric M. Lee

(57) ABSTRACT

A needle retraction mechanism includes a hollow handle defining a cavity, a needle hub assembly movably disposed in the handle, a biasing mechanism to move the needle hub assembly from an extended position to a retracted position and a latch to hold needle hub assembly in the extended position against the bias of the biasing mechanism. The needle hub assembly includes a flexible stopper at its proximal end that creates an air tight seal with the inner wall of the handle. This allows a vacuum to be created between the proximal end of the handle and the flexible stopper when the needle hub is moved from the retracted position to the extended position. The configuration of the flexible stopper allows it to change the amount of frictional force created between the inner wall of the handle and the flexible stopper when the device is at different elevations. At high elevations less frictional force exists between the inner wall of the handle and the flexible stopper while at low elevations greater frictional force exists between the inner wall of the handle and the flexible stopper.

9 Claims, 15 Drawing Sheets

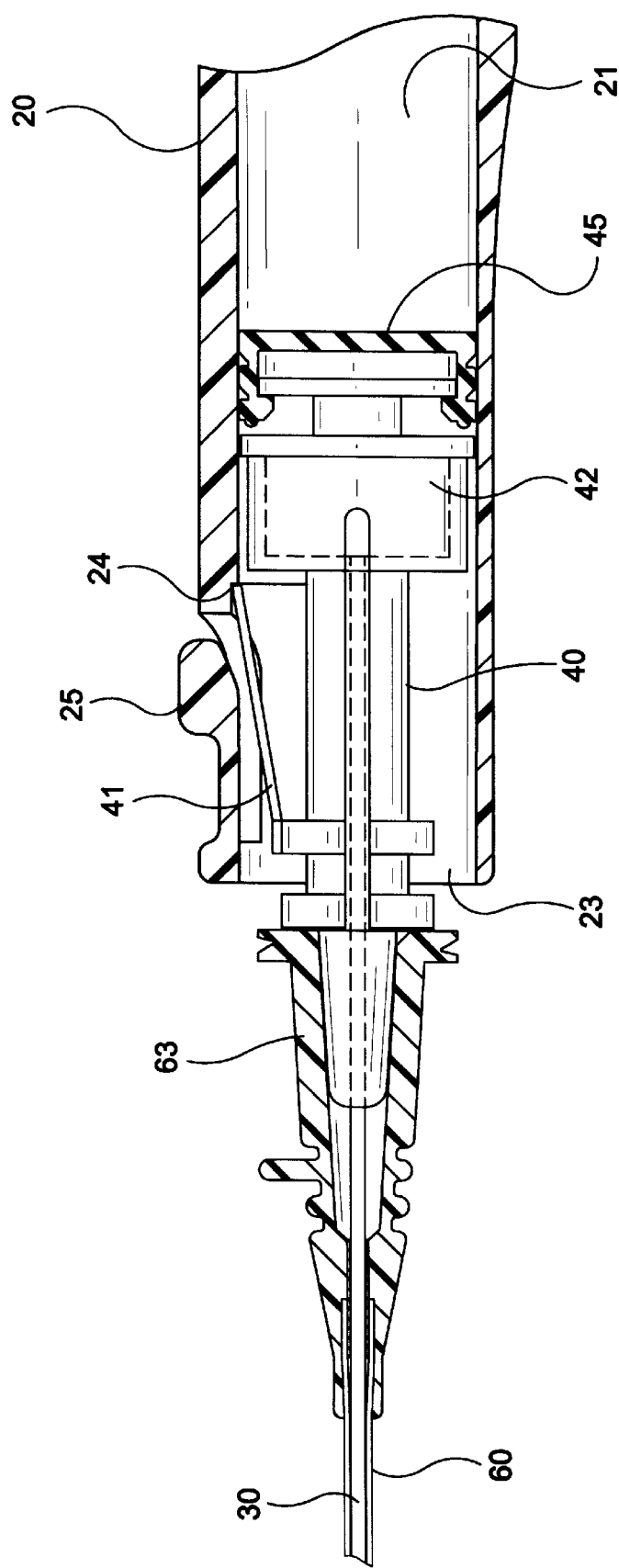

NEEDLE RETRACTION MECHANISM WITH CONTROLLED RETRACTION SPEED

This application is a continuation in part of application Ser. No. 09/164,237 filed Sep. 30, 1998, now abandoned.

BACKGROUND OF THE INVENTION

This invention generally relates to needle retraction mechanisms. More particularly, this invention relates to needle retraction mechanisms that are used in the medical field. Such needle retraction mechanisms find particular applicability in connection with intravascular catheters, syringes, blood collection tubes and lancets.

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over the needle peripheral IV catheter. As its name implies, an over the needle catheter is mounted over an introducer needle having a sharp distal tip. The catheter and the introducer needle are assembled so that the sharp distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e a smaller blood vessel that is not connected directly to the heart but is one of the branches of the central blood vessels that is directly connected to the heart. In order to verify proper placement of the assembly in the blood vessel, the clinician confirms that there is flashback of blood in the needle and in a flashback chamber located at the proximal end of the needle in conjunction with the needle hub. Once proper placement is confirmed, the clinician applies pressure to the blood vessel by pressing down on the patient's skin distal to the tip of the needle and the catheter. This finger pressure minimizes further blood flow through the catheter and needle. The clinician advances the catheter into the blood vessel, withdraws the needle, leaving the catheter in place, and attaches a fluid handling device to the catheter hub.

Once the introducer needle is withdrawn from the catheter, it is a "blood contaminated sharp" and must be properly handled. With the recognition by the medical device industry of the risk of transmission of Acquired Immunosuppressive Deficiency Syndrome (AIDS) by blood contaminated sharps, various needle shielding mechanisms have been developed. One type of a needle shielding mechanism uses a substantially hollow handle with an introducer needle movably disposed in the handle. In such a device, the sharp distal tip of the needle may be extended from a hollow handle so the sharp distal tip of the needle is exposed. After the needle has been used to place a catheter into a patient, the needle can be retracted into the handle so that the sharp distal tip of the needle is no longer exposed. Various biasing mechanisms can be used to allow the introducer needle to be retracted into the handle after use. For example, a helical spring, either in compression or tension, could be used to provide the biasing force. Alternatively, an elastic tube could be used to provide the biasing force. In order to minimize the number of parts needed for the device, a vacuum created in the proximal portion of the handle between the proximal wall of the handle and the proximal portion of the needle/needle hub can be used to provide the biasing force to retract the needle into the handle.

Although such devices generally work for their intended purpose, they could be improved. For example, it is desirable that the needle be retracted into the handle with a specific speed profile. For example, the retraction speed should not be too slow. If it is too slow the sharp distal tip of the needle will be exposed longer than is necessary after the procedure. Increased exposure time increases the risk of an accidental needle stick. On the other hand, the retraction speed should not be too fast. If the retraction speed is too fast, any blood in the needle, flashback chamber or on the exterior of the needle could become airborne during needle retraction and could be deposited outside of the handle. Such a potential blood splatter issue is especially problematic when the needle is initially removed from the catheter after the catheter has been properly placed in the patient because significant amounts of blood may have contaminated the device. This is unacceptable when the blood could be contaminated by blood borne pathogens.

Where a helical spring or an elastic tube is used as the biasing mechanism, the spring or tube can be designed to ensure that the needle is retracted with an appropriate speed within a narrow range of values. However, where a vacuum is used as the biasing mechanism, control of the retraction speed becomes problematic since the biasing mechanism is atmospheric pressure. Because the atmospheric pressure varies with altitude, the needle retraction speed varies significantly when the device is used at a location that is at sea level such as Los Angeles and New York City and when the device is used a locations that are at high altitudes such as Salt Lake City, Utah and Mexico City, Mexico. At lower elevations, the atmospheric pressure has a certain value which is greater than the atmospheric pressure at higher elevations. This results in greater force being applied against the vacuum when the device is used at lower elevations than when the device is used at higher elevations. This means that if the device is designed for use at lower elevations, the device will tend to retract the needle significantly slower when the device is used at higher elevations. Conversely, if the device is designed for use at higher elevations, the device will tend to retract the needle significantly faster when the device is used at lower elevations. And if the device is designed for used at a medium elevation, the device will tend to retract the needle too fast at lower elevations and too slowly at higher elevations. Heretofore there has not been a needle retraction mechanism that makes use of a vacuum as the biasing mechanism that can ensure that the retraction speed of the needle remains within a narrow range of values even where the device is used at low and high elevations.

SUMMARY OF THE INVENTION

It is an object of this invention to provide a needle retraction mechanism that retracts the needle at a desired speed within a narrow range of values.

It is another object of this invention to provide a needle retraction mechanism that retracts the needle at a desired speed within a narrow range of values even where the needle retraction mechansim uses a vacuum as the biasing mechanism.

It is yet another object of this invention to provide a needle retraction mechanism that retracts the needle at a desired speed within a narrow range of values when the needle retraction mechanism is used at different elevations even where the needle retraction mechanism uses a vacuum as the biasing mechanism.

The needle retraction mechanism of the present invention includes a hollow handle defining an inner wall, an outer wall and a cavity, a needle, a needle hub and a needle cover. The handle has a closed proximal end and a distal end defining an opening therein. The handle includes a release mechanism adjacent to the distal end. This release mechanism cooperates with the needle hub to hold the needle in the extended position and then to allow the needle to be retracted into the handle after the needle has been used.

The needle has an open bore therethrough with a sharp distal tip and a proximal end. The needle hub assembly is connected to the proximal end of the needle and defines a flashback chamber therein. The needle hub also includes a flexible stopper portion that engages the inner wall of the barrel and creates an air tight seal with the inner wall. The stopper ensures that a vacuum is created between the proximal end of the handle and the stopper when the needle hub is moved from the proximal end to the distal end of the handle. The stopper and needle hub are configured so the distal portion of the stopper is in communication with the opening in the distal end of the handle. This allows atmospheric pressure to be applied to the distal portion of the stopper. Additionally, the configuration of the stopper translates this atmospheric pressure so it is radially directed against the inner wall of the handle. As a result of this configuraton, the stopper exerts a relatively high radially directed force against the inner wall of the handle at lower elevations. The high radially directed force creates greater friction between the stopper and the inner wall of the handle so greater axial force is needed to retract the needle hub and needle. Thus, even though the higher pressure of the lower elevation would tend to increase the speed of retraction of the mechanism, the stopper configuration opposes this tendency. Conversely, at higher elevations, the stopper exerts a relatively low radially directed force against the inner wall of the handle and thus does not significantly interfere with the retraction speed when the retraction force will be lower.

The needle hub cooperates with the release mechanism adjacent to the distal end of the handle to hold the needle in the extended position. The needle cover is removably connected to the needle hub and is disposed over the needle. The needle cover includes a configuration that is easily grasped by a clinician to facilitate extension of the needle. When the needle retraction mechanism of the present invention is used to place a catheter into a patient, a standard catheter is located coaxially over the needle.

In the retracted position prior to use, the needle hub is adjacent to the proximal end of the handle. The handle is long enough so that the sharp distal tip of the needle does not extend past the distal end of the handle. Indeed preferably, the sharp distal tip of the needle is proximal of the distal end of the handle. This further minimizes the chance of an accidental needle stick from occurring if the needle cover is accidentally removed from the needle prior to use or after the needle has been retracted into the handle after use.

Prior to use of the needle retraction mechansim of this invention, the needle cover is disposed over the needle to shield the sharp distal tip of the needle. In addition, the needle cover is operatively connected to the needle hub with the distal portion of the needle cover extending beyond the distal end of the handle. This provides a handle for the clinician to grasp the needle cover and extend the needle so the sharp distal tip of the needle extends beyond the distal end of the handle. The needle hub includes a latch that is configured so that it engages a distally facing shoulder formed in the inner wall of the handle to temporarily lock the the needle in the extended position. Since the stopper creates an air tight seal with the inner wall, moving the needle hub distally creates a vacuum in the space between the proximal end of the handle and the needle hub. This vacuum biases the needle hub and thus the needle toward the proximal end of the handle.

When the clinician properly places the catheter into a patient, the clinician can press the release mechanism of the handle. This releases a latch on the needle hub from engagement with a distally facing shoulder in the inner wall of the handle and allows the vacuum to bias the needle hub and thus the needle toward the retracted position.

The retraction speed of the needle hub, and thus the needle, is controlled within a narrow range of values by the stopper configuration. Although the relatively high atmospheric pressure experienced at lower elevations would tend to retract the needle hub and needle at high speeds, the high radially directed force applied by the stopper against the inner wall of the handle slows down the retraction speed. Conversely, although the relatively low atmospheric pressure experienced at higher elevations would tend to retract the needle at low speeds, the low radially directed force applied by the stopper against the inner wall of the handle minimizes the slowing down of the retraction speed.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which:

FIG. 7 is an enlarged cross-sectional view of the distal portion of the needle retraction mechanism of the present invention with the needle in the extended position with one embodiment of the stopper at a low elevation and that is connected to the proximal portion of the needle hub assembly;

DETAILED DESCRIPTION OF THE INVENTION

Figure 1:
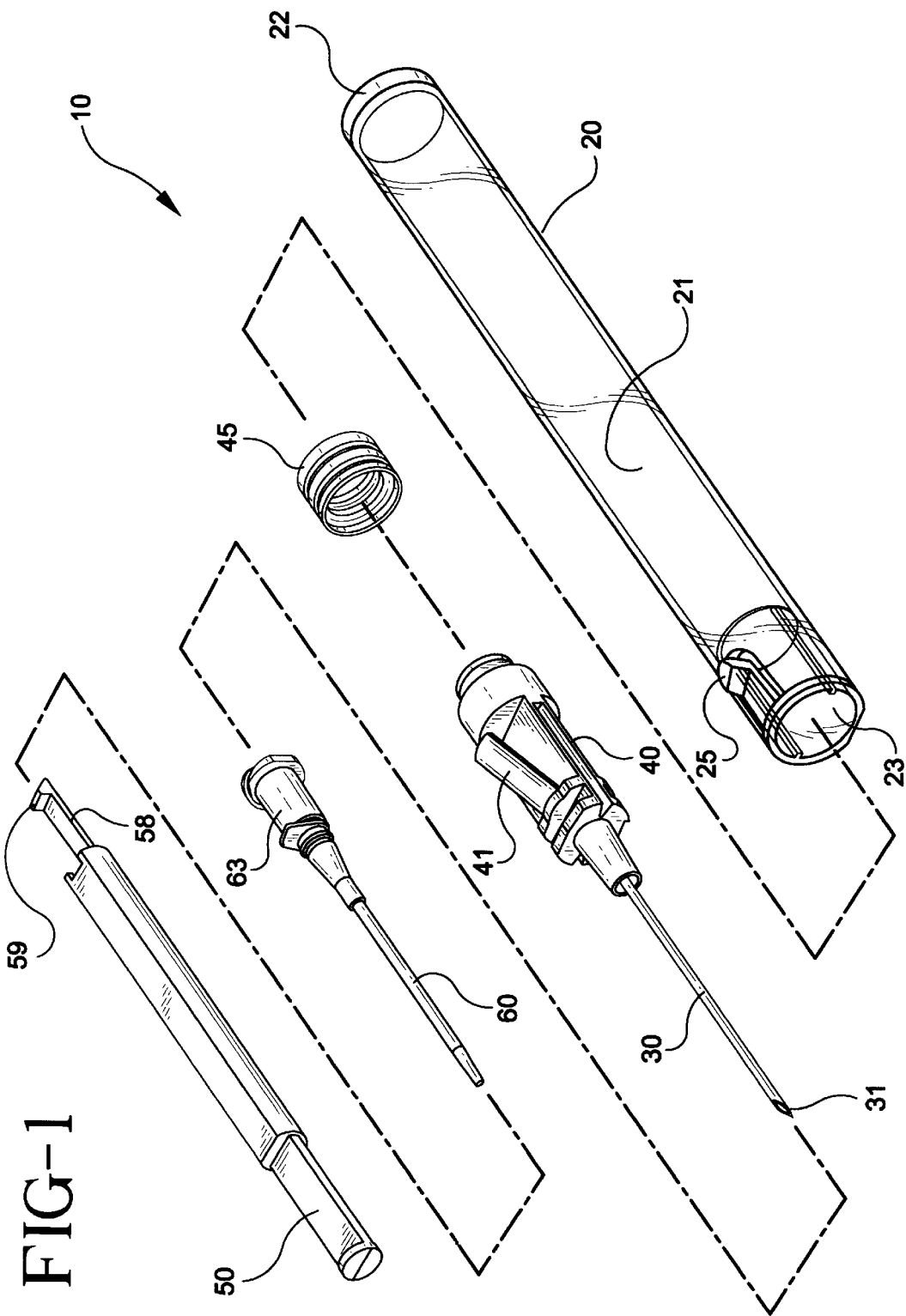
FIG. 1 is an exploded perspective view of the needle retraction mechanism of the present invention for use with an intravascular catheter.

As used herein, the term "proximal" refers to a location on the needle retraction mechanism of this invention closest to the clinician using the device and farthest from the patient in connection with whom the device is used. Conversely, the term "distal" refers to a location on the needle retraction mechanism of this invention farthest from the clinician using the device and closest to the patient in connection with whom the device is used.

Although this invention is described herein in connection with intravascular catheters, it is to be understood that this invention is applicable to other medical devices where it is desirable for a medical needle to be shielded after use. In addition, while this invention is satisfied by embodiments in many different forms, there are shown in the drawings and herein described in detail, preferred embodiments of the invention with the scope of the invention measured by the appended claims.

Figure 2:
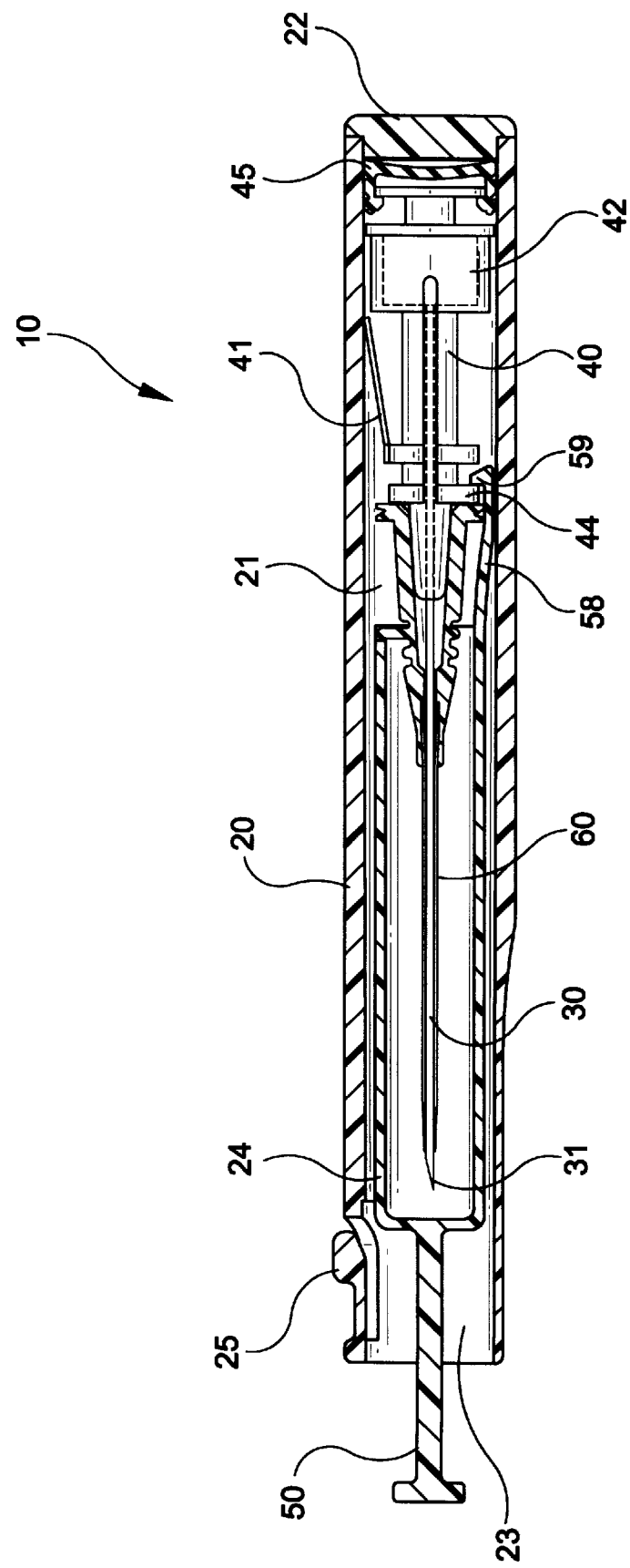
FIG. 2 is a cross-sectional view of the needle retraction mechanism of the present invention for use with an intravascular catheter with the needle in the retracted position with the needle cover still covering the needle and one embodiment of the stopper at a high elevation and that is connected to the proximal portion of the needle hub.
Figure 3:
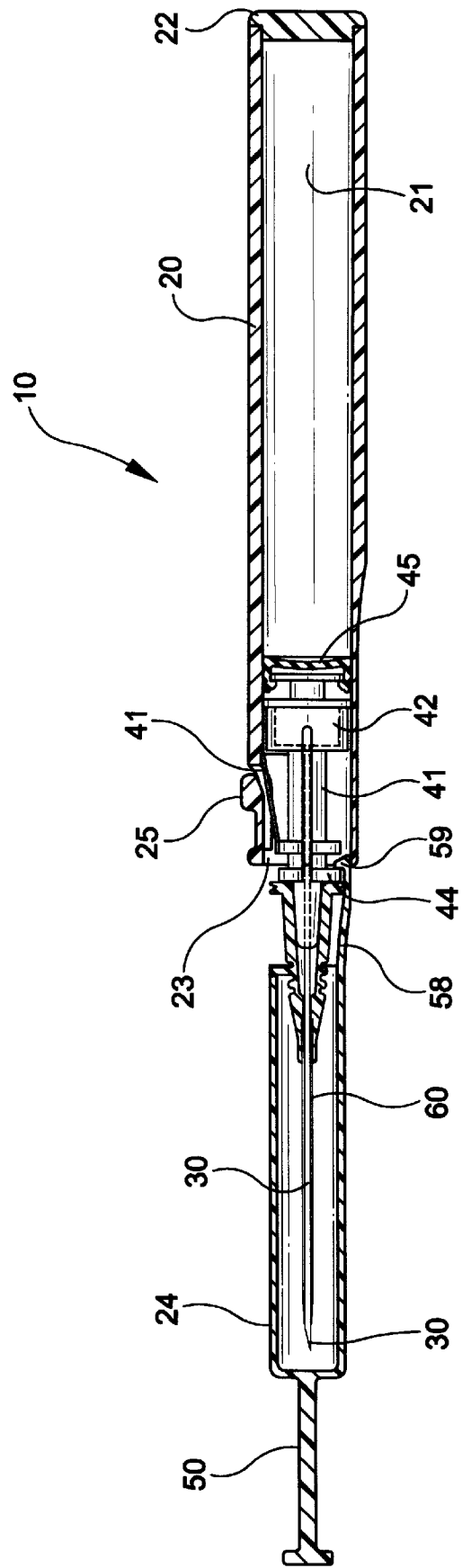
FIG. 3 is a cross-sectional view of the needle retraction mechanism of the present invention for use with an intravascular catheter with the needle in the extended position with the needle cover still covering the needle and one embodiment of the stopper at a high elevation and that is connected to the proximal portion of the needle hub.

Referring to the FIG. 1, the needle retraction mechanism 10 of the present invention includes a hollow handle 20, an elongate introducer needle 30, a needle hub assembly 40, a flexible stopper 45 connected to needle hub assembly 40, a needle cover 50 and a catheter 60. No separate biasing element is used in the present invention. Instead a vacuum created proximal of flexible stopper 45, when needle hub assembly 40 is moved from its proximal position in handle 20, see FIG. 2, to its distal position in handle 20, see FIG. 3, is used to bias needle hub assembly 40, and thus needle 30, toward the retracted postion.

Handle 20 defines an elongate cavity 21 and has a closed proximal end 22 and an open distal end 23. Suitable materials for forming handle 20 include, but are not limited to, thermoplastic polymeric resins such as polycarbonate, polystyrene, polypropylene and the like. Handle 20 is preferably formed from a substantially transparent or at least translucent material to allow a clinician to view the interior thereof.

Figure 5:
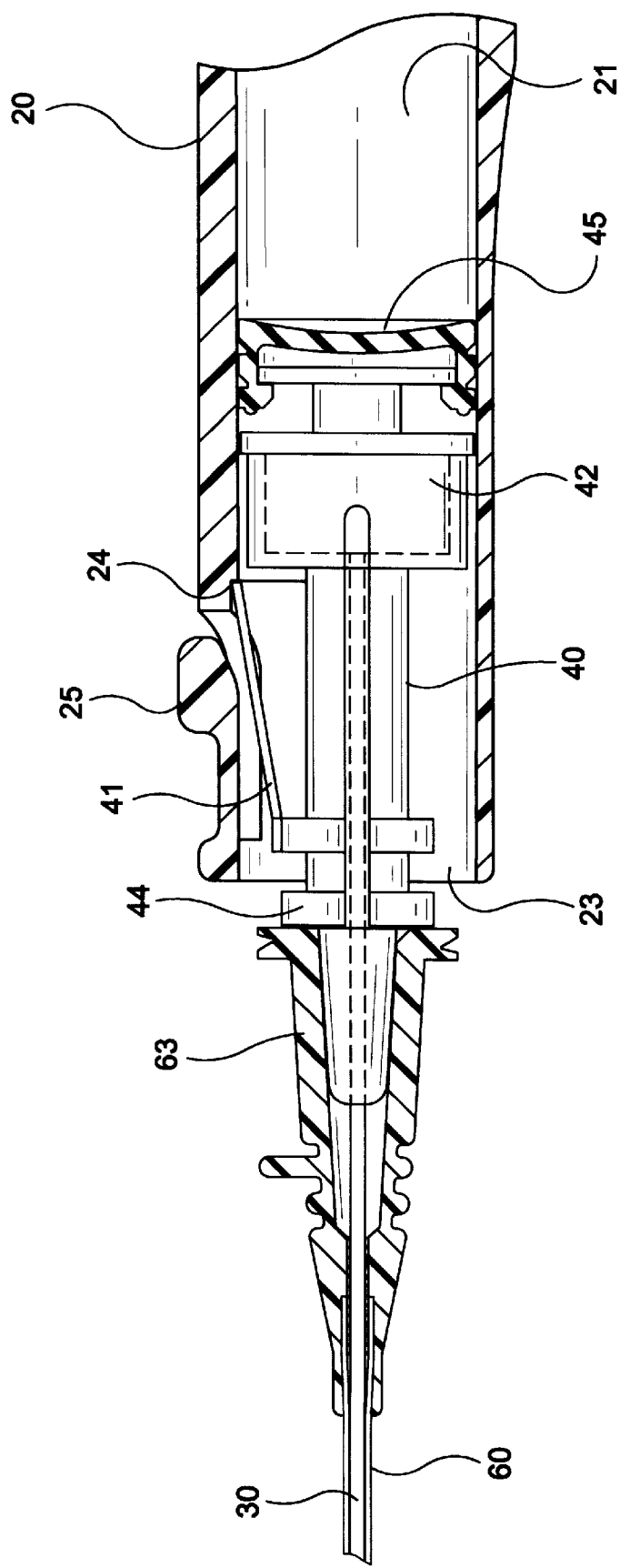
FIG. 5 is an enlarged cross-sectional view of the distal portion of the needle retraction mechanism of the present invention with the needle in the extended position with the needle cover removed and one embodiment of the stopper at a high elevation and that is connected to the proximal portion of the needle hub.

Handle 20 includes a latching mechanism that may be located along a distal portion of handle 20. The latching mechanism temporarily locks needle hub assembly 40 adjacent to distal end 23 of handle 20 against the bias of the vacuum created between flexible stopper 45 and proximal end 22 of handle 20 when flexible stopper 45 is moved distally from its retracted position. See FIG. 5. The latching mechanism can take many forms. See for example U.S. Pat. No. 5,487,734 the disclosure of which is expressly incorporated herein by reference. However, preferably the latching mechanism is a distally facing shoulder 24 formed adjacent to distal end 23 of handle 20. Distally facing shoulder 24 engages an upwardly biased flexible arm 41 movably connected to needle hub assembly 40 to temporily lock needle hub assembly 40 of the needle retraction mechanism of the present invention in the extended position against the bias of the vacuum. A tab 25 formed in and connected to the wall of handle 20 via a living hinge is used to disengage flexible arm 41 from distally facing shoulder 24 to allow needle hub assembly 40, and thus needle 30, to be retracted toward proximal end 22 of handle 20 by the bias of the vacuum.

Needle 30 typically has an open bore therethrough, although a solid needle could be used, and a sharp distal tip 31 defined by a bevel. Needle 30 is preferably formed from a stainless steel alloy or the like. Needle 30 is connected at its proximal end to needle hub assembly 40.

Needle hub assembly 40 includes flexible arm 41, a flashback chamber 42, and a flexible stopper 45. Except for flexible stopper 45, the greatest diameter of needle hub assembly 40 is less than the inner diameter of handle 20. As noted above, flexible arm 41 engages distally facing shoulder 24 when needle hub assembly 40 is adjacent to distal end 23 of handle 20. Flexible arm 41 is preferably connected to the main body portion of needle hub assembly 40 by a living hinge and is biased away from the main body portion of needle hub assembly 40. This allows flexible arm 41 to engage distally facing shoulder 24 when flexible arm 41 is distal of distally facing shoulder 24 and needle hub assembly 40 is biased to proximal end 22 of handle 20. When a clinician depresses tab 25, it forces flexible arm 41 out of engagement with distally facing shoulder 24. This allows needle hub assembly 40 and thus needle 30 to be retracted into handle 20. Suitable materials for forming needle hub assembly 40 include, but are not limited to, thermoplastic polymeric resins such as polycarbonate, polystyrene, polypropylene and the like.

As noted above, flexible stopper 45 is connected to the proximal end of needle hub assembly 40. Because the remaining portion of needle hub assembly 40 has a diameter less than the inner diameter of handle 20, the distal face of flexible stopper 45 is exposed to atmospheric pressure. Flexible stopper 45 creates an air tight seal with the inner wall of handle 20. Thus when needle hub assembly 40 is moved from its retracted position adjacent to proximal end 22 of handle 20, see FIG. 2, toward its extended position adjacent to distal end 23 of handle 20, see FIG. 3, a vacuum, or at a minimum an area that is at lower pressure than atmospheric pressure, is created in the space between flexible stopper 45 and proximal end 22 of handle 20. Suitable materials for forming flexible stopper 45 include, but are not limited to, elastomeric thermoset polymers such as polyisoprene and styrene butadiene rubber (SBR).

Figure 9:
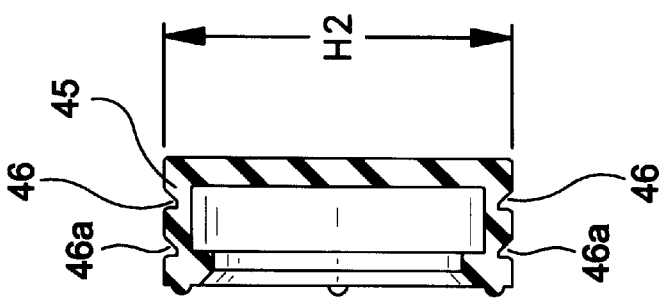
FIG. 9 is an enlarged cross-sectional view of the stopper of FIGS. 1–7 at a low elevation that is connected to the proximal portion of the needle hub assembly used in connection with the needle retraction mechanism of the present invention.
Figure 8:
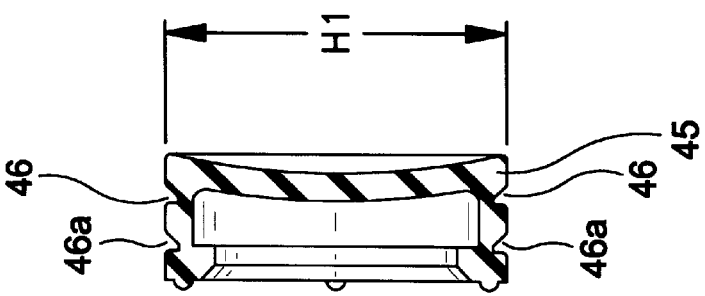
FIG. 8 is an enlarged cross-sectional view of the stopper of FIGS. 1–7 at a high elevation that is connected to the proximal portion of the needle hub assembly used in connection with the needle retraction mechanism of the present invention.

In one embodiment, flexible stopper 45 is formed with a slightly bowed configuration such that, in a relaxed state, it has a height (H1) substantially equal to the inner diameter of handle 20, and, in a biased state, it has a height (H2) that is slightly greater than the inner diameter of handle 20. At high elevation, little atmospheric pressure is directed against the distal face of flexible stopper 45 so that flexible stopper remains essentially relaxed. See FIGS. 2. 2–6 and 8. Thus, at high elevation, there is only a slight interference between flexible stopper 45 and the inner wall of handle 20 and only a slight frictional force opposing the axial movement of flexible stopper 45. This slight interference and slight frictional force does not significantly oppose the retraction force of the vacuum which will be lower due to the relatively low atmospheric pressure experienced at higher elevations. However, at low elevation the atmospheric pressure applies a greater force against the distal face of flexible stopper 45. This causes flexible stopper 45 to tend to straighten so as to increase in height just as a bow would when an axially directed force is applied to the convex face of the bow. See FIGS. 7 and 9. The greater height of flexible stopper 45 results in a greater interference between flexible stopper 45 and the inner wall of handle 20 and a greater frictional force opposing the axial movement of flexible stopper 45. Thus, although the relatively high atmospheric pressure experienced at lower elevations would tend to retract needle hub assembly 40 at high speeds, the higher frictional force applied by flexible stopper 45 against the inner wall of handle 20 slows down the retraction speed.

Figure 12:
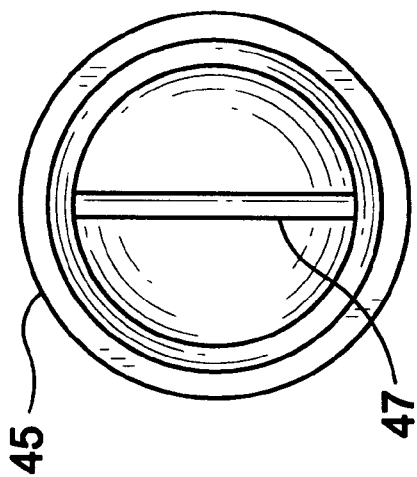
FIG. 12 is an end view of the stopper of FIG. 11 as seen from the left of FIG. 11.
Figure 11:
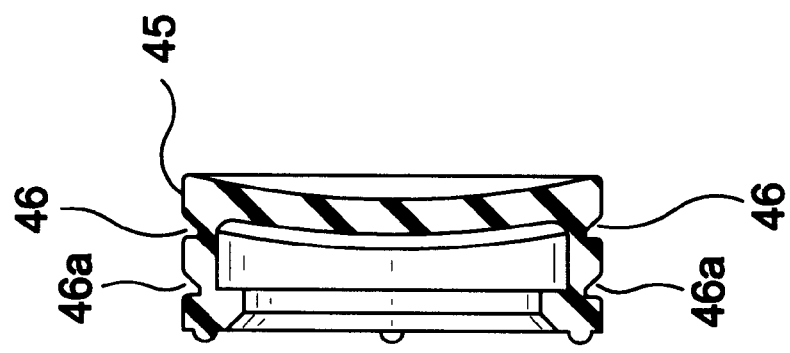
FIG. 11 is an enlarged cross-sectional view of another variation of the stopper of FIG. 8.
Figure 13:
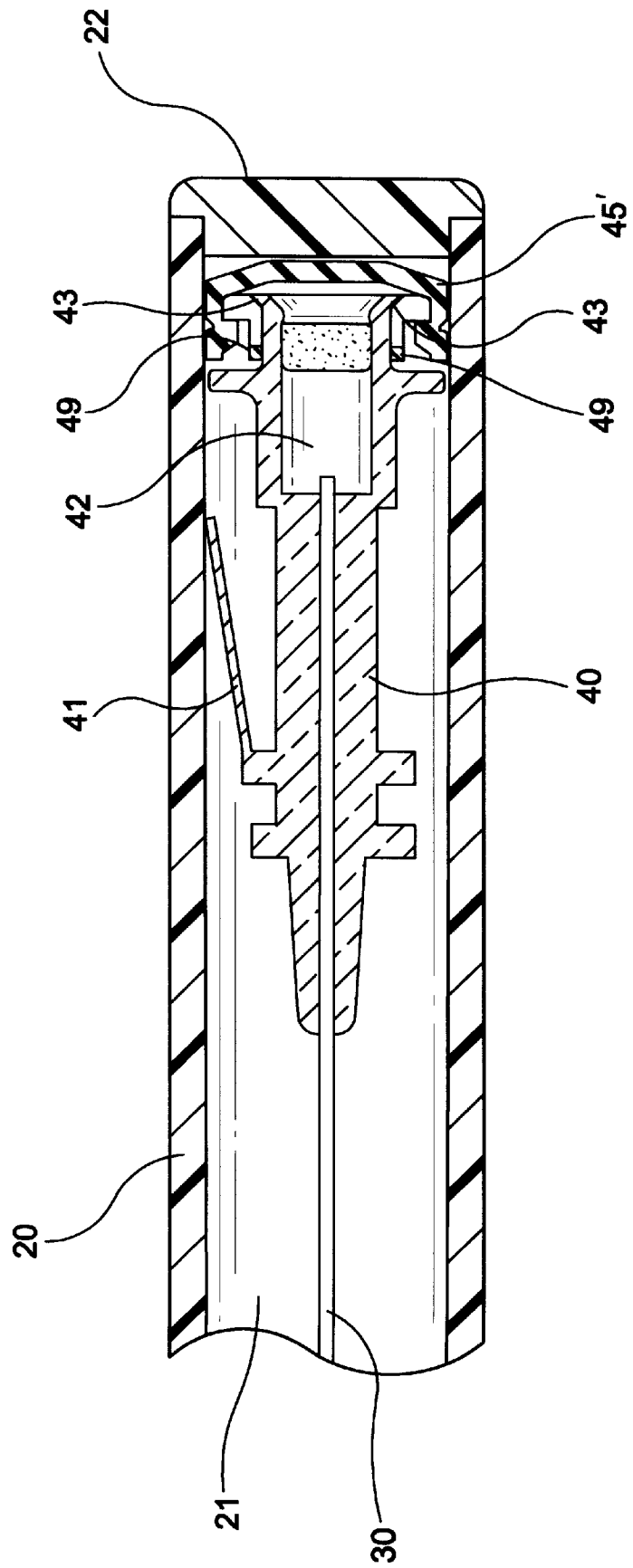
FIG. 13 is an enlarged cross-sectional view of the proximal portion of the needle retraction mechanism of the present invention with the needle in the retracted position with a second embodiment of the stopper, hub and a spring flange that is connected to the proximal portion of the needle hub assembly.

In order to facilitate the ability of flexible stopper 45 to change its height at different elevations, a hinge 46 in the form of, for example, a living hinge can be formed therein. Another mechanism to facilitate the ability of flexible stopper 45 to change its height at different locations is to use a flexible disk or rib 47 connected to one face of flexible stopper 45 or embedded in the face of flexible stopper 45. See FIGS. 11 and 12. The hinge 46 and disk or rib 47 can be used separately or together.

Preferably, a silicone oil is located in the trough 46a formed in the exterior of flexible stopper 45. In addition, silicone oil may be located in the trough formed in hinge 46. This allows flexible stopper to wipe the silicone oil against the inner wall of handle 20 as flexible stopper 45 moves therealong. It has been found that the amount and viscosity of the silicone oil in combination with the degree of interference between flexible stopper 45 and the inner wall of handle 20 affects the retraction speed for needle hub assembly 40 as it is biased toward proximal end 22 by the vacuum. When larger amounts of silicone oil are used, the retraction speed is quicker. When more viscous silicone oil is used, the retraction speed is slower. The degree of interference between flexible stopper 45 and the inner wall of handle 20 also affects the amount of force needed to overcome the static friction between flexible stopper 45 and the inner wall of handle 20 when needle hub assembly 40 is adjacent to distal end 23 of handle 20 prior to retraction of needle hub assembly 40 by the vacuum. The greater the interference, the greater the force needed to overcome this static friction. However, the amount and viscosity of the silicone oil are significantly less relevant to overcoming this static friction.

Figure 14:
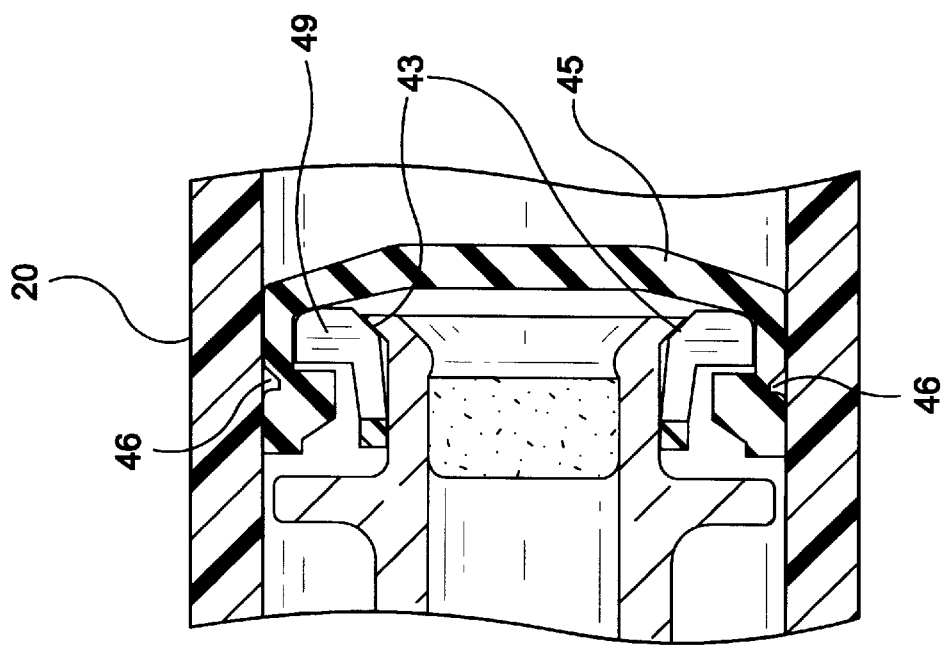
FIG. 14 is an enlarged cross-sectional view of a portion of the needle retraction mechanism of the present invention at a high elevation with the needle in the extended position with the second embodiment of the stopper, hub and a spring flange that is connected to the proximal portion of the needle hub assembly.
Figure 15:
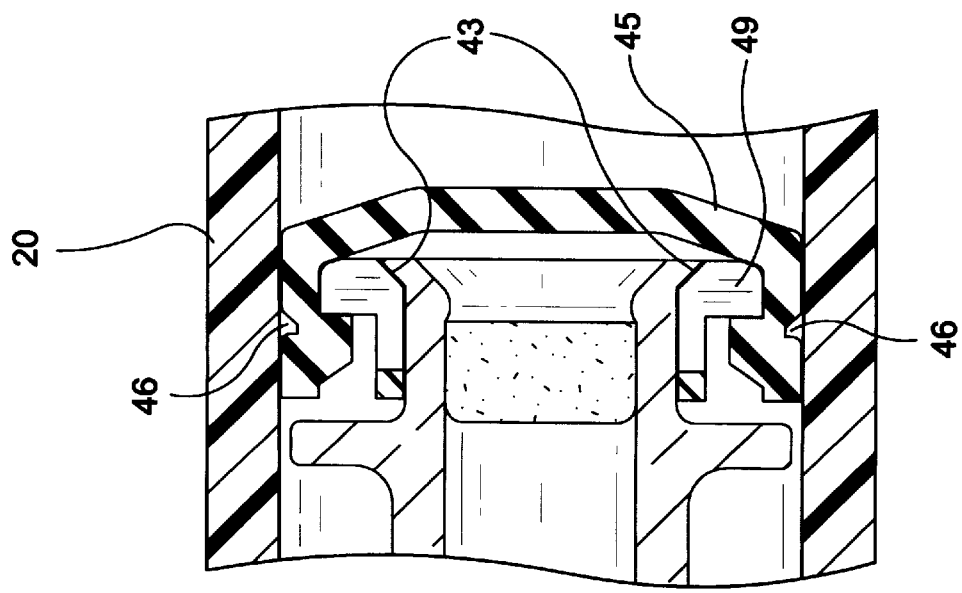
FIG. 15 is an enlarged cross-sectional view of a portion of the needle retraction mechanism of the present invention at a low elevation with the needle in the extended position with the second embodiment of the stopper, hub and a spring flange that is connected to the proximal portion of the needle hub assembly.
Figure 16:
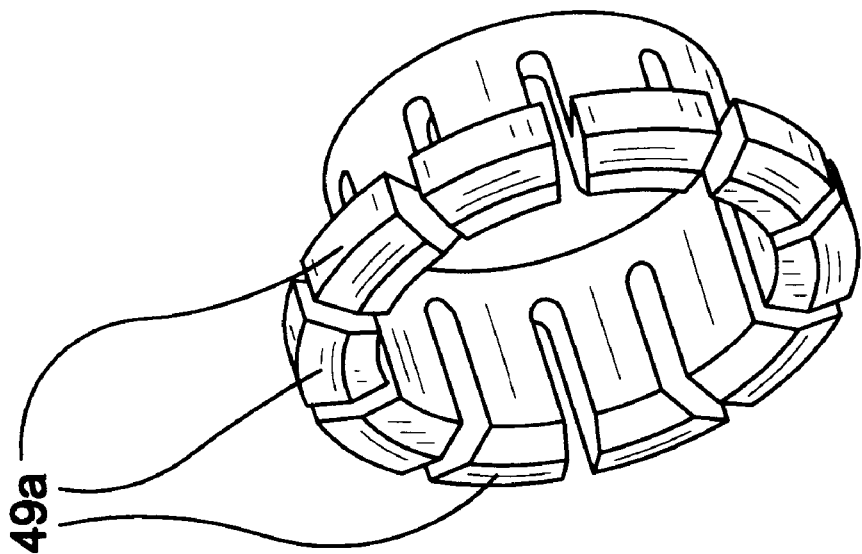
FIG. 16 is an enlarged rear perspective view of the hub and spring flange that may be used in combination with the stopper, as shown in FIGS. 13–15, that is connected to the proximal portion of the needle hub assembly used in connection with the needle retraction mechanism of the present invention.

In another embodiment, needle hub assembly 40 is formed with a ramp 43 along its proximal portion and a spring flange 49 in conjunction with flexible stopper 45'. This arrangement facilitates the translation of the axial force due to atmospheric pressure directed against flexible stopper 45' to a radial force directed against the inner wall of handle 20. Spring flange 49 is formed with a plurality of flexible fingers 49a that can move radially outwardly when spring flange 49 moves proximally over ramp 43. At high elevation, very little atmospheric pressure acts against spring flange 49. See FIG. 14. Thus at high elevations flexible fingers 49a do not bear against flexible stopper 45' with any significant force. However, at low elevations, the atmospheric pressure acts against spring flange 49 to move it proxmally over ramp 43. See FIG. 15. Since ramp 43 tapers outwardly, flexible fingers 49a move radially outwardly. As flexible fingers 49a move radially outwardly, they exert a radially directed force against flexible stopper 45'. This force extends toward the inner wall of handle 20 and results in a significant force opposing the retraction force generated by the vacuum.

Figure 17:
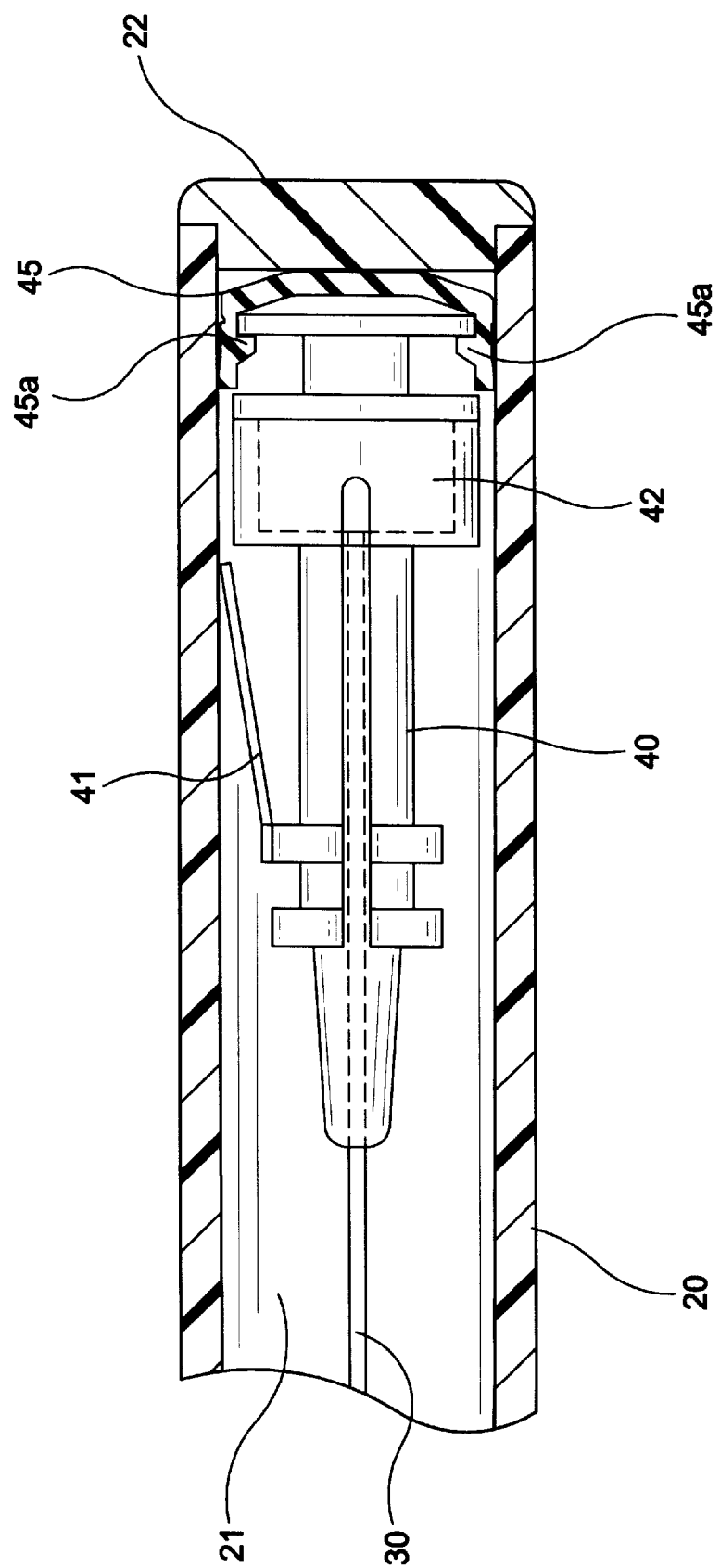
FIG. 17 is an enlarged cross-sectional view of the proximal portion of the needle retraction mechanism of the present invention with the needle in the retracted position without the spring flange of FIGS. 13–16.

Alternatively, flexible stopper 45' can be used without spring flange 49. See FIG. 17. In this embodiment, atmospheric pressure alone is used to increase the radially directed force from flexible stopper 45'. At high elevations, since there is less atmospheric pressure being applied to flexible stopper 45' less force, both axially directed and radially directed, acts on the flanges 45a of flexible stopper 45'. This minimizes the frictional force between flexible stopper 45' and the inner wall of handle 20. At low elevations, since there is greater atmospheric pressure applied to flanges 45a of flexible stopper 45' more force, both axially directed and radially directed, acts on flexible stopper 45". This increases the frictional force between flexible stopper 45' and the inner wall of handle 20. Thus at high elevations, less force opposes the retraction force of the vacuum, while at low elevations, more force opposes the retraction force of the vacuum.

Figure 18:
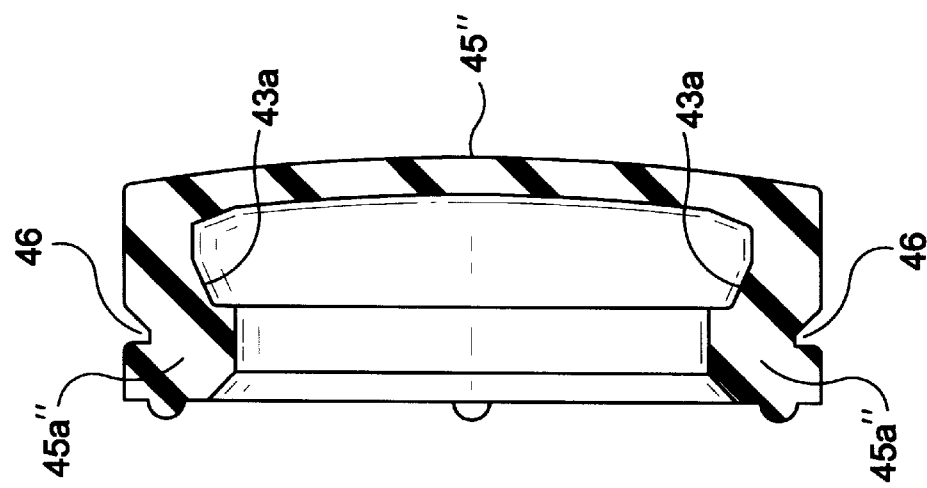
FIG. 18 is an enlarged cross-sectional view of a third embodiment of the stopper of this invention.
Figure 20:
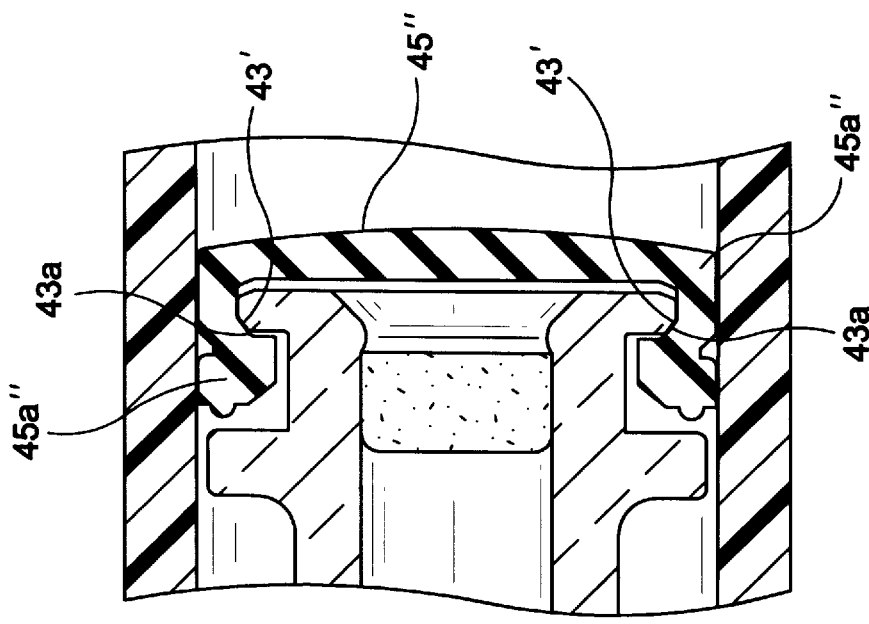
FIG. 20 is an enlarged cross-sectional view of a portion of the needle retraction mechanism of the present invention at a low elevation with the needle in the extended position with the third embodiment of the stopper that is connected to the proximal portion of the needle hub assembly.
Figure 19:
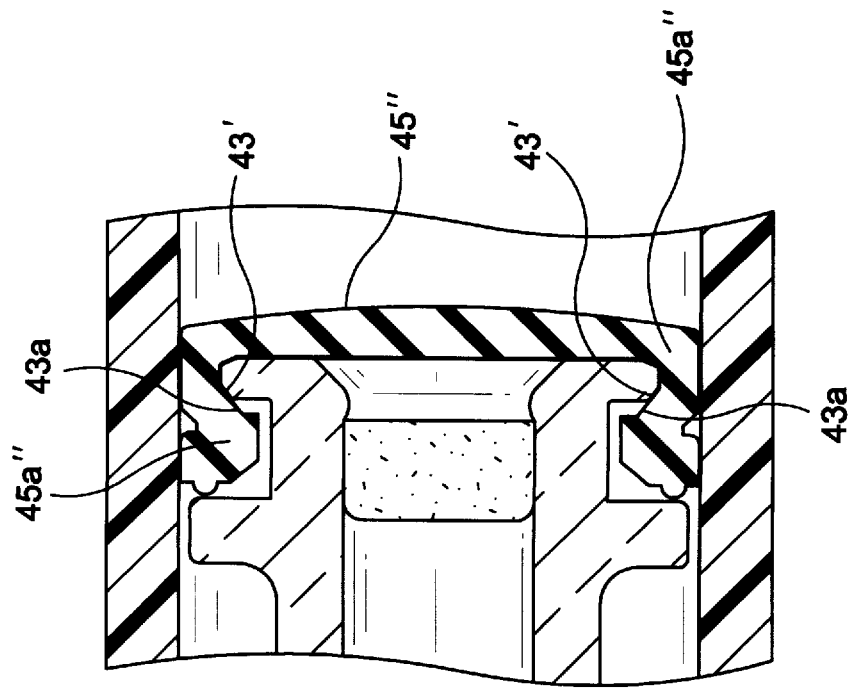
FIG. 19 is an enlarged cross-sectional view of a portion of the needle retraction mechanism of the present invention at a high elevation with the needle in the extended position with the third embodiment of the stopper that is connected to the proximal portion of the needle hub assembly.

Another embodiment of flexible stopper 45" is shown in FIGS. 18–20. In this embodiment, the proximal portion of needle hub assembly 40 includes a ramp 43' that cooperates with a ramp 43a on flexible stopper 45" to facilitate the translation of the axial force due to atmospheric pressure directed against flexible stopper 45" to a radial force directed against the inner wall of handle 20. With this configuration no spring flange 49 is required. At high elevation, very little atmospheric pressure acts against flexible stopper 45". See FIG. 19. However, at low elevations, the atmospheric pressure acts against flexible stopper 45" to move it proxmally over ramp 43'. See FIG. 20. Since ramp 43a tapers outwardly and cooperates with ramp 43a on flexible stopper 45", flanges 45a" move radially outwardly. As flanges 45a" move radially outwardly, they exert a radially directed force against the inner wall of handle 20 and results in a significant force opposing the retraction force generated by the vacuum.

Needle cover 50 is removably connected to needle hub assembly 40 and is sized and shaped to fit over needle 30 and within handle 20. The purpose of needle cover 50 is two fold. First, needle cover 50 serves to prevent accidental contact with sharp distal tip 31 of needle 30 prior to insertion of needle 30 into a patient. Second, needle cover 50 serves as a handle connected to needle hub assembly 40 to allow a clinician to move needle hub assembly 40 distally to a position adjacent to open distal end 23 of handle 20. When needle hub assembly 40 is in this position it is "armed" and ready for use. Suitable materials for forming needle cover 50 include, but are not limited to, thermoplastic polymeric resins such as polycarbonate, polystyrene, polypropylene and the like.

Figure 4:
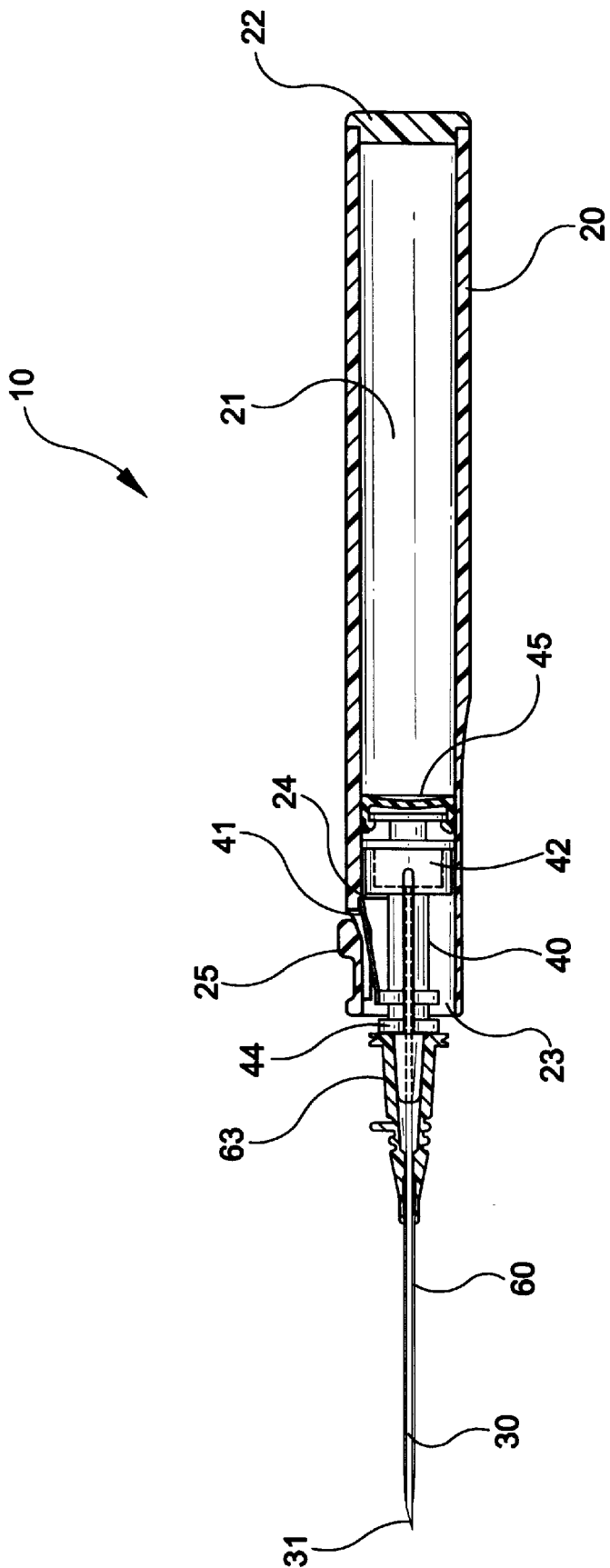
FIG. 4 is a cross-sectional view of the needle retraction mechanism of the present invention for use with an intravascular catheter with the needle in the extended position with the needle cover removed and one embodiment of the stopper at a high elevation and that is connected to the proximal portion of the needle hub.

Needle cover 50 should be sufficiently long so that when needle hub assembly 40 is adjacent to proximal end 22, the distal portion of needle cover 50 exends distally beyond distal end 23 of handle 20. See FIG. 2. This makes it easy for the clinician to move needle hub assembly 40 distally. The proximal portion of needle cover 50 is formed with an arm 58 and an upwardly extending finger 59. Finger 59 engages the proximal face of flange 44 and thus pulls needle hub assembly 40 in the distal direction when needle cover 50 is pulled distally. The distal portion of needle hub assembly 40, the distal portion of handle 20, arm 58 and finger 59 must be appropriately configured so that finger 59 will stay engaged with flange 44 until the proximal end of flexible arm 41 is distal of distally facing shoulder 24 but will become disengaged with flange 44 after the proximal end of flexible arm 41 is distal of distally facing shoulder 24. See FIG. 3. Preferably arm 58 is biased outwardly from needle hub assembly 40 so that when the proximal end of flexible arm 41 is distal of distally facing shoulder 24, arm 58 and finger 59 are no longer constrained against outward movement by handle 20. At that point finger 59 will become disengaged from flange 44 and needle hub assembly 40 will be temporarily locked adjacent to distal end 23 of handle 20 by virtue of the engagement between flexible arm 41 and distally facing shoulder 24 against the bias of the vacuum created between proximal end 22 of handle 20 and flexible stopper 45. See FIGS. 4 and 5.

A catheter 60 that has a proximal end, a distal end and a catheter hub 63 affixed to catheter proximal end is mounted over needle 30 so that the distal end of catheter 60 is proximal of sharp distal tip 31 of needle 30. Suitable materials for catheter 60 include thermoplastic resins such as fluorinated ethylene propylene (FEP), polyurethane and the like. Preferably, catheter 60 is formed from a thermoplastic hydrophilic polyurethane that softens with exposure to physiological conditions present in the patient's body. Suitable materials for catheter hub 63 include, but are not limited to, thermoplastic polymeric resins such as polycarbonate, polystyrene, polypropylene and the like.

In order to place a catheter into a patient's blood vessel, the clinician grasps the distal portion of needle cover 50 and pulls it so as to move needle hub assembly 40 toward distal end 23 of needle 20. When the proximal end of flexible arm 41 is distal of distally facing shoulder 24, finger 59 becomes disengaged from flange 44 so that needle cover 50 no longer shields needle 30. At this point, the proximal end of flexible arm 41 engages distally facing shoulder 24 to temporarily lock needle hub assembly 40 adjacent to distal end 23 of handle 20 so sharp distal tip 31 of needle 30 and catheter 60 extend beyond distal end 23 of handle 20. See FIG. 4. This distal movement of flexible stopper 45 with needle hub assembly 40 creates a vacuum in the space between proximal end 22 of handle 20 and flexible stopper 45. The clinician can then substantially longitudinally align needle 30 and catheter 50 with the target blood vessel. The bevel of needle 30 should be facing substantially away from the skin surface during venipuncture. The clinician inserts needle 30 and catheter 60 at a shallow angle, preferably less than about 35 degrees, into the skin so that sharp distal tip 31 enters the target blood vessel. The clinician then preferably observes a blood flashback in flashback chamber 42.

Figure 6:
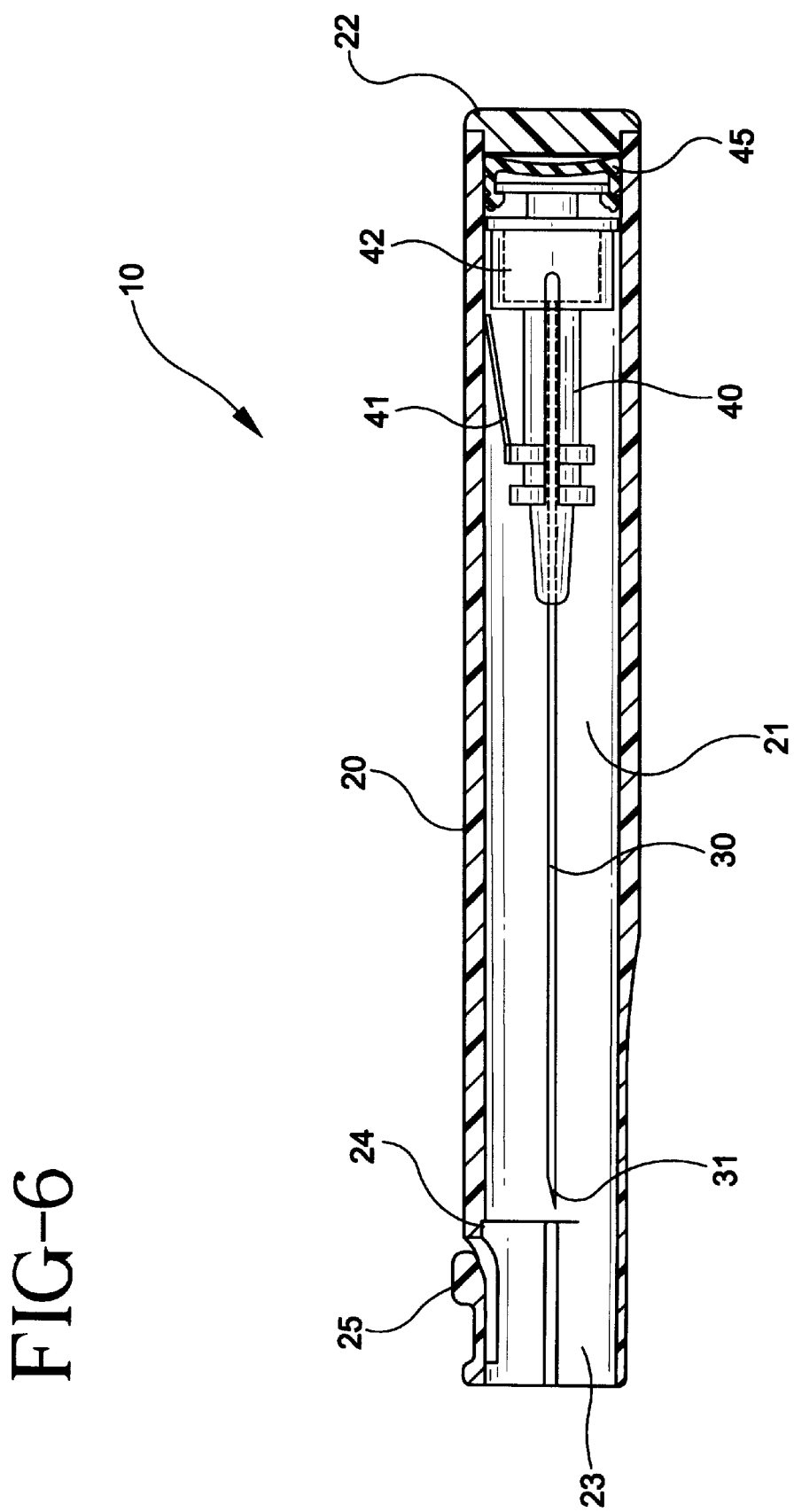
FIG. 6 is a cross-sectional view of the needle retraction mechanism of the present invention for use with an intravascular catheter with the needle in the retracted postion and the needle cover removed and one embodiment of the stopper at a high elevation and that is connected to the proximal portion of the needle hub.
Figure 10:
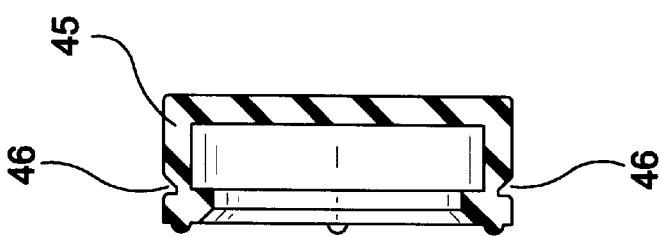
FIG. 10 is an enlarged cross-sectional view of a variation of the stopper of FIG. 8.

After confirming placement of needle 30 and catheter 60 in the target blood vessel, the clinician advances catheter 60 distally axially along needle 30 into position in the blood vessel. After proper placement of catheter 60 is achieved, the clinician places a finger from his other hand on the patient's skin over the blood vessel distal of the distal end of catheter 60 and sharp distal tip 31 of needle 30. By placing his finger on the patient's skin and applying sufficient pressure on the skin, the clinican thereby minimizes blood flow through catheter 60. The clinican then withdraws needle 30 from catheter 60 by depressing tab 25. Depressing tab 25 forces flexible arm 41 toward needle hub assembly 40 and out of engagement with distally facing shoulder 24. This allows the vacuum to urge needle hub assembly 40, and thus needle 30, into the retracted position within needle 20. See FIG. 6. The clinician may then attach any desired fluid handling device to catheter hub 63 and commence the planned treatment. Handle 20 with needle 30 substantially within it may then be disposed of according to the facility's disposal protocol.

Thus it is seen that a needle retraction mechanism is provided that retracts the needle at a desired speed within a narrow range of values even where the needle retraction mechansim uses a vacuum as the biasing mechanism.

We claim:

1. A needle retraction device, comprising:
    a handle having a proximal portion and a distal portion and defining a cavity having an inner diameter, the handle having a proximal end and a distal end defining an opening therein;
    a needle with a proximal end and a sharp distal point;
    a needle hub connected to the needle and having a proximal portion and a distal portion, the needle hub being movably disposed in the handle;
    a stopper affixed to the proximal portion of the needle hub wherein the stopper defines a first height at one elevation substantially equal to the inner diameter and defines a second height at a second elevation greater than the first heigh;
    a biasing mechanism disposed in the handle to move the needle hub from an extended position to a retracted position; and
    a latch associated with the needle hub to releasably hold the needle in the extended position.

2. The needle retraction device of claim 1 wherein the stopper has a bowed configuration in an unbiased state.

3. A needle retraction device, comprising:
    a handle having a proximal portion and a distal portion and defining a cavity having an inner diameter, the handle having a proximal end and a distal end defining an opening therein;

a needle with a proximal end and a sharp distal point;

a needle hub connected to the needle and having a proximal portion and a distal portion, the needle hub being movably disposed in the handle;

a stopper affixed to the proximal portion of the needle hub wherein the stopper exerts a first radially directed force against the handle at one elevation and exerts a second radially directed force against the handle at a second elevation;

a biasing mechanism disposed in the handle to move the needle hub from an extended position to a retracted position; and a latch associated with the needle hub to releasably hold the needle in the extended position.

4. The needle retraction device of claim 3 further comprising a hinge formed in the stopper.

5. The needle retraction device of claim 3 further comprising a reinforcing member affixed to the stopper.

6. The needle retraction device of claim 4 further comprising a reinforcing member affixed to the stopper.

7. A needle retraction device, comprising:

a handle having a proximal portion and a distal portion and defining a cavity having an inner diameter, the handle having a proximal end and a distal end defining an opening therein;

a needle with a proximal end and a sharp distal point;

a needle hub connected to the needle and having a proximal portion and a distal portion wherein the proximal portion has a diameter greater than a diameter of the distal portion and wherein the needle hub is movably disposed in the handle;

a spring flange movably disposed about the proximal portion of the needle hub;

a stopper affixed to the spring flange;

a biasing mechanism disposed in the handle to move the needle hub from an extended position to a retracted position; and a latch associated with the needle hub to releasably hold the needle in the extended position.

8. The needle retraction device of claim 7 wherein the proximal portion of the needle hub is tapered.

9. The needle retraction device of claim 7 wherein the spring flange defines a plurality of radially outwardly moveable fingers.

* * * * *